United States Patent
Yu (10) Patent No.: US 9,597,144 B2
(45) Date of Patent: Mar. 21, 2017

(54) CAUTERY

(71) Applicant: CIXI SHUN YE MEDICAL CO., LTD, Cixi, Ningbo (CN)

(72) Inventor: Dingfeng Yu, Ningbo (CN)

(73) Assignee: Cixi Shun Ye Medical Co., Ltd., Cixi, Ningbo (CN)

( * ) Notice: Subject to any disclaimer, the term of this patent is extended or adjusted under 35 U.S.C. 154(b) by 0 days.

(21) Appl. No.: 14/723,625

(22) Filed: May 28, 2015

(65) Prior Publication Data

US 2016/0058273 A1 Mar. 3, 2016

(30) Foreign Application Priority Data

Aug. 29, 2014 (CN) .......................... 2014 1 0437954

(51) Int. Cl.
| | | |
|---|---|---|
| *A61B 1/06* | (2006.01) | |
| *A61B 18/14* | (2006.01) | |
| *A61B 19/00* | (2006.01) | |
| *A61B 18/08* | (2006.01) | |
| *A61B 17/00* | (2006.01) | |
| *A61B 18/00* | (2006.01) | |

(52) U.S. Cl.
CPC ........ *A61B 18/1477* (2013.01); *A61B 18/082* (2013.01); *A61B 19/5202* (2013.01); *A61B 90/30* (2016.02); *A61B 2017/00734* (2013.01); *A61B 2018/00172* (2013.01); *A61B 2018/00178* (2013.01)

(58) Field of Classification Search
CPC ....... A61B 1/06; A61B 17/32; A61B 18/1477; A61B 19/5202; A61B 2018/00958

USPC .............. 606/37, 39, 40, 41, 42, 45, 49, 50; 219/233; 600/249

See application file for complete search history.

(56) References Cited

U.S. PATENT DOCUMENTS

| | | | | |
|---|---|---|---|---|
| 1,496,438 | A | * | 6/1924 | Wallerich ............... A61B 18/10 200/61.58 R |
| 2008/0147058 | A1 | * | 6/2008 | Horrell .............. A61B 18/1402 606/37 |
| 2011/0288543 | A1 | * | 11/2011 | Cheng ................ A61B 18/1233 606/41 |
| 2015/0216618 | A1 | * | 8/2015 | Jayaraj ............... A61B 19/5202 600/249 |

(Continued)

*Primary Examiner* — Pedro Philogene
*Assistant Examiner* — David C Comstock
(74) *Attorney, Agent, or Firm* — McKee, Voorhees & Sease, PLC (57) ABSTRACT

The invention discloses a cautery and belongs to the field of machine design. The cautery comprises a body and a replaceable cutter head. The body comprises an electric coagulation head, a switch unit and a power supply. One end of the electric coagulation head is connected with one end of the switch unit. The other end of the switch unit is connected with the power supply. One end of the electric coagulation head is connected with the power supply through the switch unit. The switch unit controls connection and disconnection between the power supply and the electric coagulation head. A heating wire is arranged on the replaceable cutter head. The replaceable cutter head is detachably connected with the other end of the electric coagulation head. By the adoption of the technical scheme, the cautery is simple in structure, easy to realize.

9 Claims, 6 Drawing Sheets

(56) References Cited

U.S. PATENT DOCUMENTS

2015/0359581 A1* 12/2015 Albertal ................ A61B 18/08
606/49

* cited by examiner

CAUTERY

CROSS REFERENCE TO RELATED APPLICATIONS

This application claims priority to Chinese Application No. 2014104.37954.9 filed Aug. 29, 2014, herein incorporated by reference in its entirety.

BACKGROUND OF THE INVENTION

1. Field of the Invention

The invention relates to a cautery and belongs to the field of machine design, especially, relates to a reusable cautery with light source.

2. Description of the Related Art

The regular monopolar cautery supplied to physician is an ideal hemostasis tool, which is easy to operate, has good hemostatic effect, has small volume, has light weight, is easy to take and is safe and flexible to use, it applies to hemostasis, tissue coagulation, neoplasm cauterization in superficial minor operation and so on. For example, cautery is used for hemostasis in eye plastic surgery, pouch removal, facelift and lift operation, and other operations having hemostasis on vein capillary vessel whose diameter is no more than 1 mm.

At present, the regular cautery is disposable, or the heating wire of it can not be replaceable. The general configuration of cautery includes a handheld device embracing cylinder shell of one or more batteries, typically, the metal wire end is electrical connected with the battery. The cautery is operated based on the on-off status of the microcircuit in the cautery controlled by switches or buttons.

After being utilized, the discarded cautery is a potential safety hazards before the battery thereof is moved. Furthermore, as it is not reusable, it will bring great disadvantages including waste of the resource and pollution of the environment. Moreover, as the heating wire can not be replaceable from the cautery, it has safety hazards when the heating wire is not removed after being utilized. For example, as the heating wire is wholly connected with the cautery, when it is discarded or placed improper, and the switch is stuck or pressed by foreign matter, the heating wire is continuous working, and it causes fire; when the disinfection is not done or done completely, it is easy to cause cross infection.

Meanwhile, the regular cautery cannot be used outdoors at night or in a working environment with insufficient light.

SUMMARY OF THE INVENTION

In respect to the cautery in the art which can not be used repeatedly, the present invention discloses a cautery.

To achieve the above purpose, the technical schemes are as follows,

A cautery, wherein comprises a body and a replaceable cutter head, the body comprises an electric coagulation head, a switch unit and a power supply, one end of the electric coagulation head is connected with one end of the switch unit, the other end of the switch unit is connected with the power supply, one end of the electric coagulation head is connected with the power supply through the switch unit, the switch unit controls connection and disconnection between the power supply and the electric coagulation head, a heating wire is arranged on the replaceable cutter head, the replaceable cutter head is detachably connected with the other end of the electric coagulation head.

Preferably, a connector is configured on the replaceable cutter head, a jack which is fitted to the connector is configured on the other end of the electric coagulation head, the replaceable cutter head is detachably connected with the electric coagulation head by the matching between the connector and the jack.

Preferably, the body comprises a main post and a number of batteries configured in serials in the main post.

Preferably, one end of the main post is connected with the electric coagulation head, a rear cover is configured on the other end of the main post, the rear cover is connected with the main post by thread.

Preferably, one end of the batteries in the main post is connected with the electric coagulation head, the other end of the batteries is connected with the rear cover.

Preferably, comprising a conduction band and a button, the other end of the batteries is connected with one end of the conduction band, the other end of the conduction band is connected with the electric coagulation head by the button.

Preferably, a groove is configured on the main post, the button is configured in the groove of the main post, a switch fulcrum is configured in the groove of the main post, a button fulcrum, which is fitted to the switch fulcrum, is configured on one end of the button, the other end of the conduction band passes through and is configured between the button fulcrum and the switch fulcrum, a switch clip is configured on the other end of the button.

Preferably, an elastic element is configured between the other end of the batteries and the rear cover, the other end of the batteries is connected with one end of the conduction band by the elastic element and the rear cover.

Preferably, the main post is connected with the rear cover by the thread, a rabbet is configured on the thread connected between the main post and the rear cover, a bulge, which is fitted to the rabbet, is configured on the conduction band, the conduction band is configured between the main post and the rear cover by the matching between the bulge and the rabbet, the conduction band is connected with the rear cover.

Preferably, further comprises an illuminating device, the illuminating device is configured on the electric coagulation head, and the illuminating device is connected with the power supply by the switch unit.

Compared to the prior art, the technical schemes of the invention make it possible for the battery and the heating wire to be replaced and also possible for the heating wire to be removed swiftly when it is out of work so that potential safety hazards and producing cost are both reduced. Furthermore, the cautery disclosed by the present invention is also suitable for use outdoors at night or in a working environment with insufficient light.

BRIEF DESCRIPTIONS OF THE DRAWINGS

The drawing of the present invention is provided a further understanding of the invention, the embodiments and the explanation of the invention are used to illustrate the invention, and it is not interpreted to the scope of the invention. In the drawings.

DETAILED DESCRIPTION OF THE PREFERRED EMBODIMENT

The technical scheme is described clearly and completely by the following embodiments in combination with the drawings. It is obviously that the embodiments described are only a part of the embodiments of the invention, and they are not the full embodiments. Based on the embodiments of the invention, the other all embodiments obtained by the skilled in the art without working creatively are in the scope of the invention.

It is need to be indicated that the embodiments and feature of the embodiments can be combined to each other.

The embodiments are described by the following embodiments in combination with the drawings.

Figure 1:
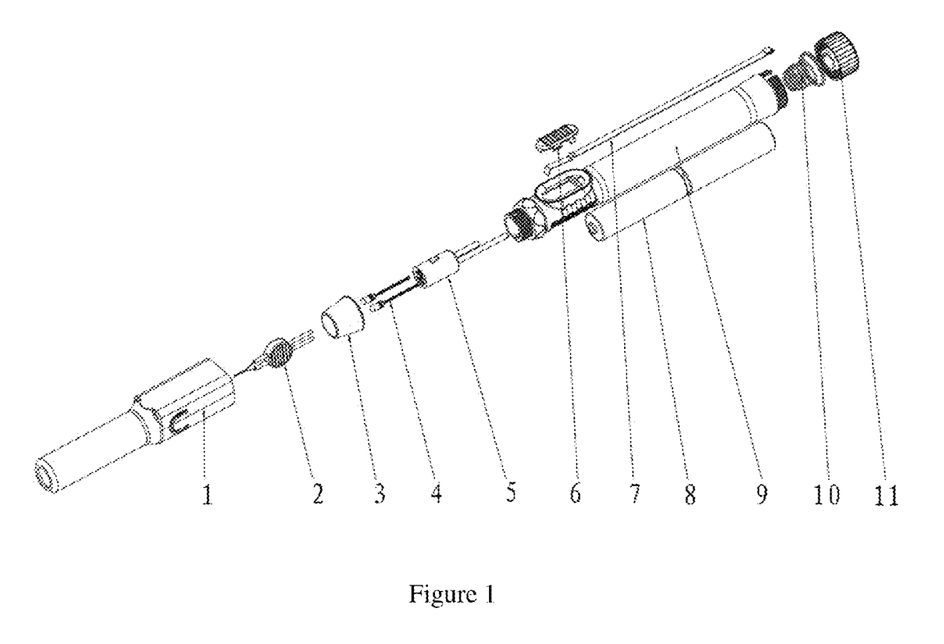
FIG. 1 is a structure schematic diagram of an embodiment according to the invention.
Figure 2:
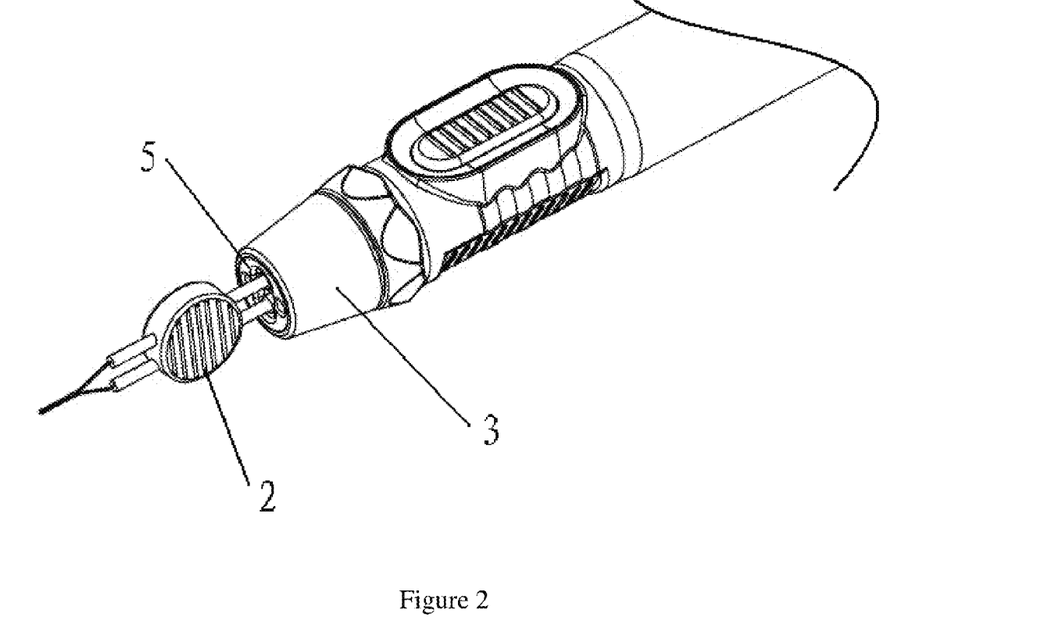
FIG. 2 is a structure schematic diagram of the replaceable cutter head in an embodiment according to the invention.

Referring to FIGS. 1 to 2, a cautery disclosed by this embodiment comprises a body and a replaceable cutter head 2. The body comprises an electric coagulation head 5, a switch unit and a power supply. One end of the electric coagulation head 5 is connected with one end of the switch unit. The other end of the switch unit is connected with the power supply. One end of the electric coagulation head 5 is connected with the power supply through the switch unit. The switch unit controls connection and disconnection between the power supply and the electric coagulation head 5. A heating wire is arranged on the replaceable cutter head 2. The replaceable cutter head 2 is detachably connected with the other end of the electric coagulation head 5.

The embodiment of the invention is simple in structure, easy to realize, capable of reducing potential safety hazards and cost, and the heating wire can be replaced, and the heating wire can be removed when it is out of work.

Referring to FIG. 1, in this embodiment of the invention, the cautery comprises a head cap 1, a replaceable cutter head 2, a metal fixed head 3, a micro bulb 4, an electric coagulation head 5, a button 6, a conduction band 7, a battery 8, a main post 9, a spring 10 and a rear cover 11. A elastic clip is configure on the two sides of the head cap 1, which enables the head cap 1 to be clipped in the main post 9 to protects the head of the electric coagulation device.

Referring to FIGS. 2 to 1, a connector is configured on the replaceable cutter head 2, a jack matching with the connector is configured on the other end of the electric coagulation head 5, the replaceable cutter head 2 is detachably connected with the electric coagulation head 5 by the matching between the connector and the jack. The electric coagulation head 5 is fixed on the body by the metal fixed head 3 in the front end. In the embodiment, the connection structure of the electric coagulation head 5 is a split type structure, and it is easy to assemble; the electric coagulation head 5 is made of heat-resisting material, to prevent the device from working abnormally caused by the damage to the electric coagulation head 5 due to heat from the heating wire with high temperature during a continuous work.

Furthermore, the connection tube (metal contact tube) in the electric coagulation head 5, which is the jack, is indent type. When it is not working, bending deformation of the connection tube (metal contact tube) or the disconnection between the connection tube (metal contact tube) and the replaceable cutter head 2 due to the bending deformation of the connection tube (metal contact tube) will not occur even if the even if it falls down or crashes unexpectedly. Furthermore, referring to FIG. 3, a fixing bulge 15 is configured on two sides of the electric coagulation head 5, a gap 16 is configured on the main post 9, and the electric coagulation head 5 is fixed correctly in a direction by the matching between the fixing bulge 15 and the fixing gap 16.

Figure 4:
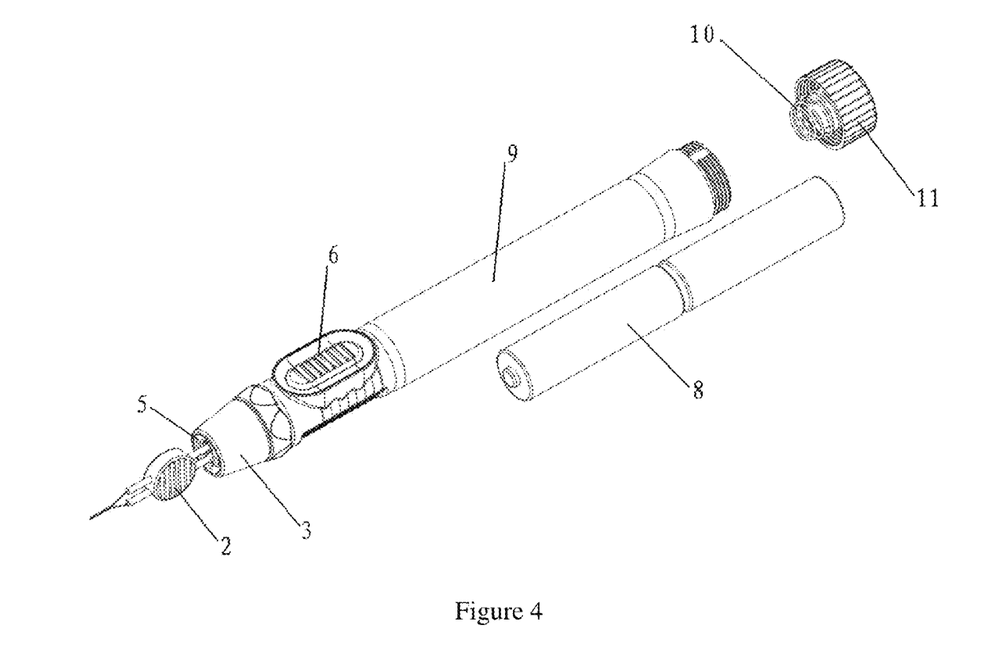
FIG. 4 is a structure schematic diagram of the body in an embodiment according to the invention.

Referring to FIG. 4, in the embodiment of the invention, the body comprises a main post 9 and a number of batteries 8 configured in series in the main post 9. One end of the main post 9 is connected with the electric coagulation head 5, a rear cover 11 is configure on the other end of the main post 9, the rear cover 11 is connected with the main post 9 by thread, the battery 8 can be replaced by taking down the rear cover. Preferably, the battery 8 is an alkaline battery, or a lithium battery which can be repeatedly charged.

One end of the batteries 8 in the main post 9 is connected with the electric coagulation head 5, the other end of the batteries 8 is connected with the rear cover 11 by the spring 10.

Figure 3:
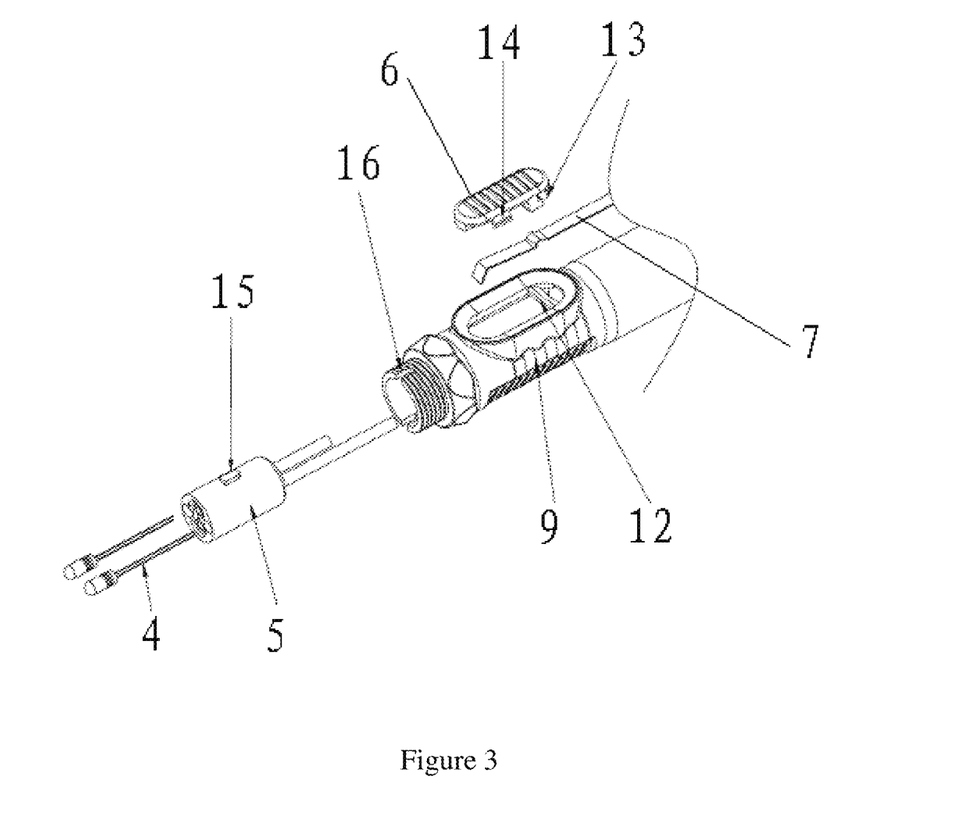
FIG. 3 is a structure schematic diagram of the button in an embodiment according to the invention.

Furthermore, referring to FIG. 1 and FIG. 3, in the embodiment of the invention, the conduction band 7 and the button 6 are also comprised. The other end of the batteries 8 is connected with one end of the conduction band 7, the other end of the conduction band 7 is connected with the electric coagulation head 5 by the button 6, the button 6 controls the connection and disconnection between the battery 8 and the electric coagulation head 5. Preferably, the button 6 is an inner concave structure with respect to the body, when the electric coagulation device is placed horizontally or it is rolled, the switch button will not be touched so that accidental operation of the electric coagulation device can be avoided. Reference is made in combination with FIG. 3, a groove is configured on the main post 9, the button 6 is configured in the groove of the main post 9, to prevent the switch from being touched by accident.

Referring to FIG. 3, a switch fulcrum 12 is configured in the groove of the main post 9, a button fulcrum 13 matching with the switch fulcrum 12 is configured on one end of the button 6. When being assembled, the other end of the conduction band 7 passes through and is configured between the button fulcrum 13 and the switch fulcrum 12. Furthermore, a switch clip 14 matching with the groove of the main post 9 is configured on the other end of the button 6.

The button 6 in this embodiment comprises a rear part and a front part, the rear part is an independence fulcrum, the front part is connected with the main post 9 through a clip structure, the switch button moves up and down on the fulcrum, thus the structure is simple, the assembling is easy, and the operation is flexible. Meanwhile, the switch fulcrum 12 configured in the groove of switch hole of the main post 9 matches with the button fulcrum 13, and the conduction band 7 is fixed in the main post 9 stably.

Figure 5:
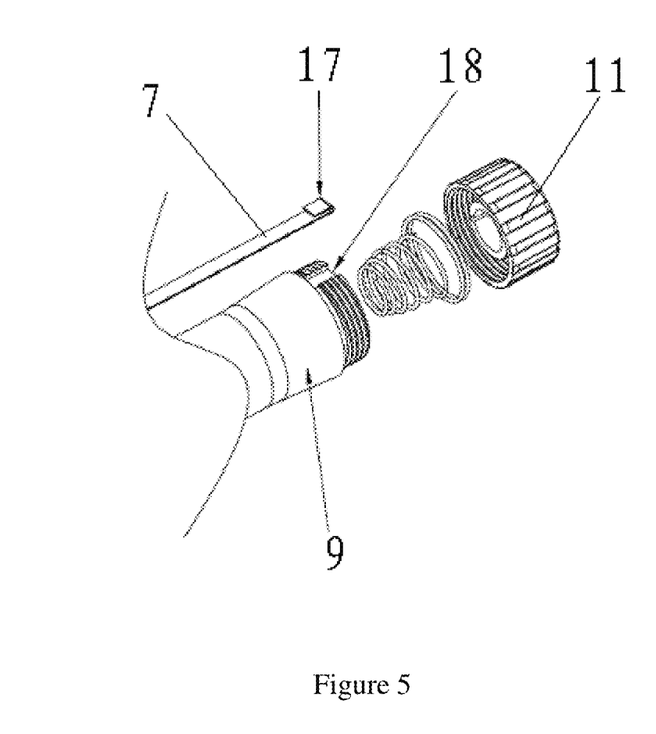
FIG. 5 is a structure schematic diagram of the rear cover in an embodiment according to the invention.

Referring to FIG. 5, in the embodiment of the invention, the main post 9 is connected with the rear cover 11 by thread. A rabbet 18 is configured in the thread connected between the main post 9 and the rear cover 11. A bulge 17 matching with the rabbet 18 is configured on the conduction band 7. The conduction band 7 is configured between the main post 9 and the rear cover 11 by the matching between the bulge 17 and the rabbet 18, and the conduction band 7 is connected with the rear cover 11. Reference is made in combination with FIG. 2, the other end of the batteries 8 is connected with one end of the conduction band 7 by the spring 10 and rear cover 11.

Figure 6:
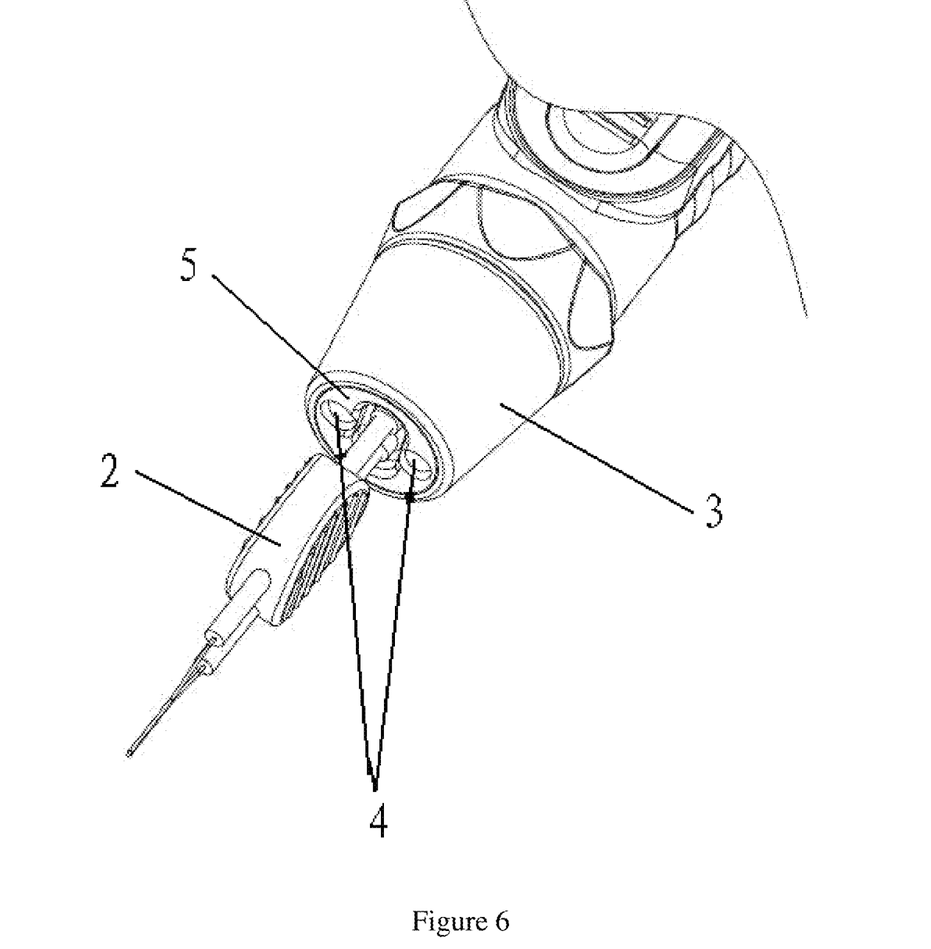
FIG. 6 is a structure schematic diagram of the illuminating device in an embodiment according to the invention.

Referring to FIGS. 1, 3 and 6, in the embodiment of the invention, there is an illuminating device. Preferably, they are two micro bulbs 4 whose outer diameter is 3 mm. The micro bulb 4 is planted into the electric coagulation head 5.

When the cautery is working, the light source is then lighted, to provide local lighting. It can reduce the requirement of the light in the working environment if additional light is provided by the embedded micro bulb.

The explanation above is only the detailed description for the embodiments of the invention, it is used as examples and the invention is not limited in the above embodiments. For the skilled in the art, any various of changes and modifications are in the scope of the invention. It is therefore intended that such changes and modifications be covered in the scope of the invention without apart from the spirit and the scope of the invention.

What is claimed is:

1. A cautery comprising:
   a body, said body comprising an electric coagulation head having a first end and second end, a switch unit having a top end and a bottom end, and a power supply;
   a replaceable cutter head detachably connected to the first end of electric coagulation head;
   a heating wire is arranged on the replaceable cutter head;
   a conduction band extending between the electric coagulation head and the power supply;
   wherein the second end of the electric coagulation head is connected with the top end of the switch unit;
   wherein the bottom end of the switch unit is connected with the power supply;
   wherein the second end of the electric coagulation head is connected with the power supply through the switch unit;
   wherein the switch unit further comprises a button, the button configured to control the connection and disconnection between the power supply and the electric coagulation head;
   wherein conduction band is connected with the electric coagulation head by the button; and
   wherein the button is an inner concave structure with respect to the body.

2. The cautery as disclosed in claim 1, wherein a connector is configured on the replaceable cutter head, a jack which is fitted to the connector is configured on the other end of the electric coagulation head, the replaceable cutter head is detachably connected with the electric coagulation head by the matching between the connector and the jack.

3. The cautery as disclosed in claim 2, wherein the body comprises a main post and one or more batteries configured in serial in the main post.

4. The cautery as disclosed in claim 3, wherein one end of the main post is connected with the electric coagulation head, a rear cover is configured on the other end of the main post, the rear cover is connected with the main post by threads.

5. The cautery as disclosed in claim 4, wherein one end of the one or more batteries configured in serial in the main post is connected with the electric coagulation head, the other end of the one or more batteries configured in serial is connected with the rear cover.

6. The cautery as disclosed in claim 5, wherein a groove is configured on the main post, the button is configured in the groove of the main post, a switch fulcrum is configured in the groove of the main post, a button fulcrum, which is fitted to the switch fulcrum, is configured on one end of the button, the other end of the conduction band passes through and is configured between the button fulcrum and the switch fulcrum, a switch clip is configured on the other end of the button.

7. The cautery as disclosed in claim 6, wherein an elastic element is configured between the other end of the batteries and the rear cover, the other end of the batteries is connected with one end of the conduction band by the elastic element and the rear cover.

8. The cautery as disclosed in claim 7, wherein the main post is connected with the rear cover by the thread, a rabbet is configured on the thread connected between the main post and the rear cover, a bulge, which is fitted to the rabbet, is configured on the conduction band, the conduction band is configured between the main post and the rear cover by the matching between the bulge and the rabbet, the conduction band is connected with the rear cover.

9. The cautery as disclosed in claim 8, further comprises an illuminating device, the illuminating device is configured on the electric coagulation head, and the illuminating device is connected with the power supply by the switch unit.

* * * * *